(12) United States Patent
Zimmermann

(10) Patent No.: US 6,592,886 B1
(45) Date of Patent: Jul. 15, 2003

(54) PRODUCING STABLE CROSS-LINKED ALGINATE GEL BY BINDING SURPLUS CATIONS WITH ANIONS

(75) Inventor: Ulrich Zimmermann, Waldbrunn (DE)

(73) Assignee: CellMed AG, Alzenau (DE)

( * ) Notice: Subject to any disclaimer, the term of this patent is extended or adjusted under 35 U.S.C. 154(b) by 0 days.

(21) Appl. No.: 09/492,212

(22) Filed: Jan. 27, 2000

(30) Foreign Application Priority Data

Feb. 5, 1999 (DE) .......................................... 199 04 785

(51) Int. Cl.[7] .............................. A61F 2/00; A61K 9/50; C12N 11/10; C12N 5/06; C12N 5/08
(52) U.S. Cl. ....................... 424/423; 424/93.7; 424/490; 424/491; 435/178; 435/382
(58) Field of Search .................................. 434/174, 177, 434/178; 424/423, 93.7, 491, 490; 435/382

(56) References Cited

U.S. PATENT DOCUMENTS

| | | | |
|---|---|---|---|
| 4,409,331 A | * 10/1983 | Lim ........................... | 435/178 |
| 4,781,676 A | * 11/1988 | Schweighardt et al. ....... | 604/21 |
| 5,429,821 A | 7/1995 | Dorian et al. ............... | 424/424 |
| 5,718,862 A | * 2/1998 | Thompson .................. | 264/296 |
| 6,365,385 B1 | * 4/2002 | Opara ........................ | 435/178 |
| 6,375,985 B1 | * 4/2002 | Bomberger et al. ......... | 424/489 |

FOREIGN PATENT DOCUMENTS

| | | |
|---|---|---|
| DE | 44 26 396 | 2/1996 |
| DE | 187 07 910 | 9/1998 |

OTHER PUBLICATIONS

F.Lim et al. in "Science", vol. 210, Nov. 1980, p. 908–910; "Microencapsulated Islets as Bioartificial Endocrine Pancreas".

H.A. Clayton et al., in "Acta Diabetol.", vol. 30, 1993, p. 181–189; "Islet microencapsulation: a review".

T.Zekorn et al. in "Acta Diabetol.", vol. 29, 1992, p.99–106; "Barium–cross–linked alginate beads: a simple, one–step method for successful immunoisolated transplantation of islets of Langerhans".

P. DeVos et al. in "Biomaterials", vol. 18, 1997, p. 1085–1090; "Upscaling the production of microencapsulated pancreatic islets".

C.Hasse et al. in "Exp. Clin. Endocrinol. Diabetes", vol. 105, 1997, p.53–56; "Isotransplantation of microencapsulated parathyroid tissue in rats".

"J. Microencapsulation", vol. 14, No. 5, 1997, p. 617–626; "First successful xenotransplantation of microencapsulated human parathyroid tissue in experimental hypoparathyroidism: long–term function without immunosuppression".

U.Zimmerman et al. in "Electrophoresis", vol. 13, 1992, p. 269–274; "Production of mitogen–contamination free alginates with variable ratios of mannuronic acid to guluronic acid by free flow electrophoresis".

G.Klock et al. in "Biomaterials", vol. 18, 1997, p. 707–713; "Biocompatibility of mannuronic acid–rich alginates".

C.Hasse et al. in "The Lancet", vol. 350, 1997, p. 1296; "Parathyroid allotransplantation without immunosuppression".

P. de Voss et al. in "Diabetologia", vol. 40, 1997, p. 262–270; "Improved biocompatibility but limited graft survival after purification of alginate for microencapsulation of pancreatic islets".

P. Grohn et al. in "Exp. Clin. Endocrinol.", vol. 102, 1994, p. 380–387; "Large–scale production of Ba2+–alginate–coated islets of Langerhans for immunoisolation".

P. Grohn et al. "BioTechniques", vol. 22, May 1997, p. 970–975; "Collagen–Coated Ba2+–Alginate Microcarriers for the Culture of Anchorage–Dependent Mammalian Cells".

\* cited by examiner

*Primary Examiner*—David M. Naff
(74) *Attorney, Agent, or Firm*—Nields & Lemack

(57) ABSTRACT

A stable cross-linked alginate gel such as in the form of alginate gel beads encapsulating transplant materials is produced by binding surplus multivalent cations remaining after cross-linking alginate with the cations. A cross-linked alginate gel containing the surplus cations is contacted with a solution of multivalent anions such as sodium sulfate solution to bind the surplus cations. Preferably, a dehydration preventing agent such as protein, bone powder or implant substances is present during cross-linking. A hydrophobic substance such as a perfluoro hydrocarbon or an emulsion may be present during cross-linking to fill spaces between alginate chains. Alginate gel beads produced by the process have long term stability after transplanting.

15 Claims, 1 Drawing Sheet

PRODUCING STABLE CROSS-LINKED ALGINATE GEL BY BINDING SURPLUS CATIONS WITH ANIONS

BACKGROUND OF THE INVENTION

The subject of the invention is the production of polymer alginate material, especially the production of alginate beads or films, the use of such alginate materials and biological implants that are enclosed in or coated with such alginate materials.

It is known that, with allogene or xenogene transplantations, immune responses of the host organism can be countered by microencapsulation of the transplant for the purpose of immunoisolating it (see F. Lim et al. in "Science", vol. 210, 1980, pp 908–910, H. A. Clayton et al. in "Acta Diabetol.", vol. 30, 1993, pp 181–189). Spherical alginate beads have proven their advantages in encapsulating allogene or xenogene, endocrine tissue (for example see T. Zekorn et al. in "Acta Diabetol.", vol. 29, 1992, pp 41–52, P. De Vos et al. in "Biomaterials", vol. 18, 1997, pp 273–278, C. Hasse et al. in "Exp. Clin. Endocrinol. Diabetes", vol. 105, 1997, pp 53–56, and in "J. Microencapsulation", vol. 14, 1997, pp 617–626). The alginates are $Ca^{2+}$ or $Ba^{2+}$ linked and especially effective in immuno-isolation if they are purified, ie as free as possible of mitogeneous contamination (see U. Zimmermann et al. in "Electrophoresis", vol. 13, 1992, pp 269–274, G. Klöck et al. in "Biomaterials", vol. 18, 1997, pp 707–713).

The transplantation of alginate encapsulated tissue is not only tested in animal experiments but is already being introduced in human medicine. Thus C. Hasse et al. in "The Lancet", vol. 350, 1997, p 1296, for example, describe microencapsulation in the case of an allogene parathyroid transplantation in the muscle tissue of two patients with permanent symptomatic hypoactivity of the parathyroid. After treatment with alginate immuno-isolated parathyroid tissue, it was possible for the patients to leave hospital without showing hypocalcaemic symptoms and without requiring therapy to suppress immune responses. Nevertheless, as before in animal experiments, the transplants were only effective for a limited time, which can be traced to the disappearance of the alginate enclosure.

From U.S. Pat. No. 5,429,821 we know of the formation of alginate coated transplants where, to increase alginate stability, $Ca^{2+}$ linked alginate gel is cross-linked with L-poly-lysine or other physiologically acceptable, non-toxic polycations. The advantage of this technique is improved alginate stability. But cross-linking with L-poly-lysine is nevertheless a disadvantage, because the embedded transplant can trigger fibrosis, resulting in problems as in the use of unpurified alginates. Consequently, further treatment of the alginate gels is necessary to achieve biocompatibility of the transplant.

The stability of the transplanted alginate beads is a general problem that is also described by G. Klöck et al. in "Biomaterials", vol. 18, 1997, pp 707–713, for example, and by P. De Vos in "Diabetologia", vol. 40, 1997, pp 262–270. Continuing clinical use of alginate encapsulated transplants calls for the development of more stable alginate beads.

SUMMARY OF THE INVENTION

The object of the invention is to propose a method for producing alginate material, especially for enclosing or coating transplants, that results in enhanced stability and reliability of the alginate material in practical conditions. It is also the object of the invention to propose new uses for such alginate material and new transplants provided with improved alginate material of this kind.

These objects are resolved by a method with the features of patent claim 1. Advantageous embodiments of the invention result from the attached claims.

DETAILED DESCRIPTION OF THE INVENTION

Figure 1:
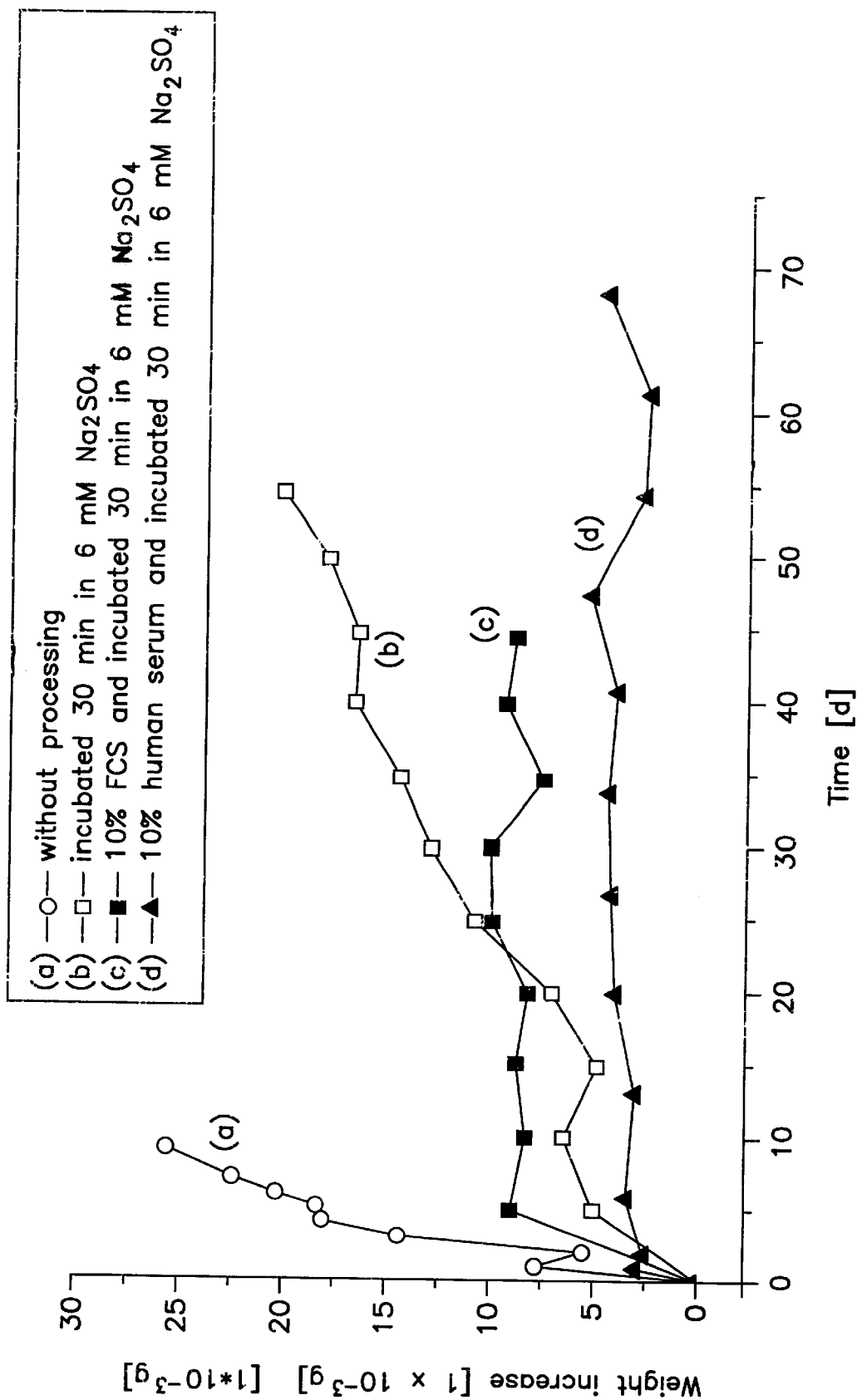
FIG. 1 is a graph showing the weight of alginate beads versus time.

The invention is based on the idea, after formation of a cross-linked alginate material by precipitation of a dissolved alginate in a precipitating solution, of exposing the alginate material to a processing solution in which the difference in chemical potential of aqueous constituents in the alginate material and the water in the processing solution or the colloidal osmotic pressure between the alginate material and the processing solution is minimized or balanced to zero. For this purpose, the solution of a substance is preferably used that binds surplus divalent cations in the alginate, like a sulfate solution (eg $Na_2SO_4$ solution), in order to bind the surplus ions in the alginate material and, simultaneously, to reduce the afore-mentioned difference in thermodynamic potential or colloidal osmotic pressure.

Processing of the cross-linked alginate material according to the invention is preferably used to produce alginate beads for encapsulating transplant materials or effective substances that are to be embedded in the human organism. Alginate beads produced according to the invention exhibit substantially higher stability compared to conventional alginate beads.

In a preferred embodiment of the invention, the cross-linked gel material is formed from a modified alginate solution. For this purpose, biologically compatible buffer substances, proteins, and/or hydrophobic substances are added to the alginate solution.

Also a subject of the invention is a composite transplant consisting of a composite core with an alginate encapsulation, whereby the composite core comprises biological cells and/or dispersed effective components, and the alginate encapsulation is produced according to the method of the invention. The biological cells are living cells producing hormones or antibodies for example. The encapsulated effective components comprise medicinally or nutritional physiologically effective substances, for instance, or possibly marker substances provided so that, after incorporation in the human organism, they can be detected by an external measuring method in relation to predetermined substance properties as a function of the particular environment.

The invention possesses the following advantages. For the first time, alginate encapsulations are created that exhibit substantially greater stability than conventional alginate encapsulations. Thus, in particular, the possibility is given for the first time of performing reproducible longterm investigations of the transplantation of alginate encapsulated substances in animal organisms or on patients.

Further details and advantages of the invention are illustrated by the following description with reference to the attached figure. FIG. 1 shows a curve of the weight of alginate beads versus time to illustrate the effect of processing linked alginate material according to the invention.

The invention is described in what follows with reference to the production of beaded alginate encapsulations for microscopic particles that are to be incorporated in a living organism. The invention is not restricted to this application however. It can also be used for the production of alginate material in other forms (eg carrier layers for cell cultures, plane encapsulating layer, intermediary layers in composite transplants, material in bandages, material in socalled functional food etc.).

The formation of cross-linked alginate material as microscopic beads is according to the processes described by P. Gröhn et al. in "Exp. Clin. Endocrinol.", vol. 102, 1994, p 380 ff, or C. Hasse et al. in "The Lancet", vol. 350, 1997, p 1296 for example. The details given there of isolating the transplant material, preprocessing the alginate, encapsulating the transplant material and purifying the encapsulated alginate material are adopted in their entirety in the present description. Production of the alginate beads is preferably performed by precipitation of an alginate solution precipitating solution containing in a divalent or multivalent ions using the two- or three-channel drop technique described in the named publication.

The alginate beads, described in what follows with reference to the measurement results in FIG. 1, were produced under the following conditions. Highly purified alginate was dissolved in a 9% NaCl solution. The viscous solution was pressed through the inner channel of a two-channel generator at a constant rate of approx. 0.2 ml/min. The size and consequently the weight of the beads was controlled by adding a coaxial stream of air. The drops of alginate solution fell into an iso-osmolar $Ba^{2+}$ solution (20 mM) with 0.72% NaCl. After about 1 min the beads were removed and washed three times with a 0.9% NaCl solution for the control sample (curve (a)) and, for the samples according to the invention, incubated for about 30 min in an iso-osmolar NaCl solution with $Na_2SO_4$ (6 mM) (curves (b) through (d)). The size and corresponding by the weight of the beads were measured to standard with a microscope (Zeiss) and precision scales (Sartorius). In the case of the samples treated according to the invention (curves (c) and (d)), this process mode was modified by adding human albumin (c) or 10% fetal calf serum (d) to the alginate and precipitating solution. These additives can also be introduced to the ambient solution in further treatment of the beads.

The invention is based on the following observations. If alginate beads, after their formation in a precipitating solution (eg with 20 mM $Ca^{2+}$ or $Ba^{2+}$ ions), are transferred to an iso-osmolar NaCl solution (T=37° C.) without an extra processing step being performed on the linked alginate material according to the invention, the result is the curve marked by circles (a) in FIG. 1. The alginate beads swell, which can be seen from the illustrated increase of mass with time. After about one week, the bead material breaks open or bursts and the beads decompose. It was established that this swelling phenomenon of the alginate beads, ultimately leading to their decomposition, depends on the presence of surplus divalent cations, which remain after the polymerization or cross-linking process in the aqueous phase of the cross-linked alginate gel matrix and cause transportation of water from the surroundings into the matrix material. The divalent cations are originally contained in the precipitating solution and, in the formation of the cross-linked alginate material, serve for saturating available free, negatively charged carboxyl groups in the gel matrix. The available free carboxyl groups are those carboxyl groups of the guluronic acid and mannuronic acid chains of the alginate that do not participate in cross-linking. The number of surplus cations remaining after cross-linking and thus the occurrence of the decomposing phenomenon described above consequently depend on the monomer composition, the block structure and the molecular weight of the alginate molecules used as starting material.

It was also established that a colloidal osmotic pressure is formed through organic buffer molecules (eg MOPS, HEPES) that are added to the precipitating solution with typical concentrations of eg 10 mM and are integrated in the gel matrix during the cross-linking process and, like the carboxyl groups, bind with the divalent cations. These bindings are characterized by relatively high electrostatic forces, so the divalent ions can barely be washed out by monovalent ions, or only very slowly. The surplus divalent cations produce the colloidal osmotic pressure however, which leads to a water take-up that triggers the aforementioned swelling of the beads.

To avoid the described water take-up of the cross-linked alginate material, the invention proposes processing the alginate material with a processing solution that is intended to produce a state of equilibrium between the aqueous solution remainders in the gel matrix and the surrounding solution as fast as possible. The processing solution preferably contains divalent or multivalent anions in order to bind the surplus cations in the gel matrix as fast as possible. The processing solution is preferably a sulfate solution, eg $Na_2SO_4$ solution, or a complexing or precipitating solution.

Processing of the cross-linked alginate material with the sulfate solution according to the invention is made for a time predetermined according to the application. Typical values for incubation time are in ranges of from 10 to 60 min for an $Na_2SO_4$ solution with concentrations in a range between 0.4 and 20 mM. The curve marked with squares (b) in FIG. 1 shows a delay in swelling of the beads to about 50 days for 30 min processing of the cross-linked alginate in a 6 mM $Na_2SO_4$ solution. Processing of the alginate material is preferably at room temperature or temperatures that are of interest in physiological terms (37° C.).

The alginate material is subjected to the processing solution immediately after cross linkage. But it is also possible, for the event that the alginate material is first dried immediately after cross-linkage, that the processing solution be added later in use of the alginate material. So, generally, the subject of the invention is also processing of cross-linked alginate material with a sulfate solution to conduct ion exchange.

Further improvement in preventing water up-take in the alginate material according to the invention is achieved if histidine or as a buffer substance another biological buffer substance is contained in the precipitating solution instead of conventional organic buffer molecules. Histidine has an isoelectric point at a pH value of 7.2. A preferred concentration range for histidine addition is about 1 to 10 mm.

The undesired swelling of the cross-linked alginate material is reduced according to the invention by further additives in the alginate solution and/or precipitating solution. This is illustrated by curves (c) and (d) in FIG. 1. Lasting stabilization of the alginate beads can be achieved by adding proteins to the alginate solution and/or precipitating solution, these being intended to prevent dehydration of the alginate during polymerization (cross linkage). Examples of such proteins are human or animal serums (eg fetal calf serum (FCS), human albumin serum or proteins from the blood of the particular patient). Preferred protein concentrations are in the range between 4 and 20%. An especially stable alginate material was produced with a 10% protein concentration in the 1% alginate solution and in the precipitating solution. Incubation of 30 min in a 6 mM $Na_2SO_4$ solution produces the curves in FIG. 1 with filled in squares (c) and triangles (d).

For clinical applications, ie transplants in patients, the concentration of the serum proteins is preferably chosen so that osmotic pressure in the particular solution is matched to the osmotic pressure of the proteins in the blood. The protein concentration is selected according to the protein concentration in the patient's blood that is to be determined beforehand. Biocompatible proteins (eg the body's own proteins) to the particular patient must be used.

Alternatively, instead of the fetal calf serum, bone powder (ground bones) or implant substances like Cementex (synthetic bone source) can be used.

To improve matrix stability, it is possible, extra to the addition of protein or as an alternative to this, to add biocompatible, hydrophobic substances or emulsions to the alginate solution and/or precipitating solution, these being intended to fill spaces between the chains of the alginate molecules during cross linkage, as a result of which the space available for the aqueous solution is reduced. Examples of such substances are perfluoro hydrocarbons. The advantage of perfluor hydrocarbons is that they have already proven their worth in medical applications and are suitable as marker substances for NMR analysis. It is possible, for example, to determine the oxygen partial pressure in an implant by non-invasive NMR measurement of the 19 F signal of perfluor hydrocarbons, and thus to produce a statement on the living conditions of the implant. One example of a hydrophobic substance is Fluorosol. If this is added in a ratio of 1:1 before cross-linkage of the alginate solution and the precipitating solution, a prolonged stability as in curves (c) and (d) is also obtained. p Compared to curve (a), curves (b) through (d) show a remarkably longer lifetime of the alginate beads. This allows transplant investigations on animal or human organism within the time frames that are of interest. Transplantation of alginate beads produced according to the invention in muscle tissue and under the kidney capsule of socalled Lewis rats has produced excellent longterm stability. It was possible, for example, to verify stability of more than two years with Fluorosol processed alginate beads.

Further advantages for bead stability are achieved if, in alginate cross-linkage, tissue or cells of the parathyroid are immobilized simultaneously to the incorporation of proteins and/or Fluorosol in alginate cross linkage.

What is claimed is:

1. Method for producing a cross-linked alginate gel matrix comprising the steps of:

contacting an alginate solution with a precipitating solution containing multivalent cations to cross-link the alginate and produce a cross-linked alginate gel matrix containing surplus multivalent cations remaining after cross-lining that do not participate in cross-linking, stabilizing the cross-linked alginate gel matrix by carrying out the cross-linking in the presence of a dehydration preventing agent to prevent dehydration of the alginate gel during cross-linking, and contacting the alginate gel matrix containing surplus cations with a processing solution containing multivalent anions that bind the surplus multivalent cations to produce said cross-liked alginate gel matrix.

2. Method according to claim 1 in which the processing solution is a sulfate solution.

3. Method according to claim 2 in which the processing solution is a sodium sulfate solution.

4. Method according to claim 1 wherein the alginate and/or precipitating solution contain biologically compatible buffer molecules.

5. Method according to claim 4 wherein said biologically compatible buffer molecules comprises histidine.

6. Method according to claim 1 wherein said dehydration preventing agent comprises at least one protein.

7. Method according to claim 6 in which said at least one protein comprises human or animal serum protein.

8. Method according to claim 7 in which said at least one protein is from a source selected from the group consisting of fetal calf serum, human albumin serum and blood of a treated patient.

9. Method according to claim 1 wherein said alginate solution and/or precipitating solution contains a biocompatible, hydrophobic substance or emulsion to fill spaces between alginate chains during cross-linking.

10. Method according to claim 9 in which the hydrophobic substance is a perfluoro hydrocarbon.

11. Method according to claim 3 in which the solution has a sodium sulfate concentration between 0.4 and 20 mM, and the solution is contacted with the alginate gel matrix for about 10 to 60 minutes.

12. Method according to claim 1, wherein said multivalent anions are divalent.

13. Method according to claim 1, wherein said dehydration preventing agent is contained in said alginate solution.

14. Method according to claim 1, wherein said dehydration preventing agent is contained in said precipitating solution.

15. Method according to claim 1, wherein said dehydration prevention agent is selected from the group consisting of bone powder and implant substances.

* * * * *